United States Patent [19]

Ohashi et al.

[11] 4,371,699

[45] Feb. 1, 1983

[54] PROCESS FOR PREPARATION OF OPTICALLY ACTIVE N-MERCAPTOALKANOYLAMINO ACIDS

[75] Inventors: Takehisa Ohashi, Kobe; Masami Shimazaki, Takasago; Kazunori Kan, Kobe; Hideo Kondo, Takasago; Kiyoshi Watanabe, Akashi, all of Japan

[73] Assignee: Kanegafuchi Chemical Industry Co., Ltd., Osaka, Japan

[21] Appl. No.: 214,780

[22] Filed: Dec. 9, 1980

[30] Foreign Application Priority Data

Dec. 13, 1979 [JP] Japan .............................. 54-162377
Dec. 13, 1979 [JP] Japan .............................. 54-162378
Dec. 28, 1979 [JP] Japan .............................. 54-171904
Mar. 8, 1980 [JP] Japan .............................. 55-29430

[51] Int. Cl.³ .................. C07D 207/16; C07D 211/60; C07D 277/06
[52] U.S. Cl. .................... 548/201; 548/200; 548/533; 548/537; 546/215; 435/146
[58] Field of Search .................... 260/326.2; 548/200, 548/201; 546/245; 435/146

[56] References Cited

U.S. PATENT DOCUMENTS

| | | | |
|---|---|---|---|
| 4,046,889 | 9/1977 | Ondetti et al. | 260/326.2 |
| 4,070,361 | 1/1978 | Petrillo, Jr. | 260/326.2 |
| 4,105,776 | 8/1978 | Ondetti et al. | 260/326.2 |
| 4,192,878 | 3/1980 | Ondetti | 548/201 |

FOREIGN PATENT DOCUMENTS 54-144252 of 1979 Japan .
54-144253 of 1979 Japan .
55-17559 of 1980 Japan .
55-103805 of 1980 Japan .
55-140258 of 1980 Japan .
55-140259 of 1980 Japan .
55-141453 of 1980 Japan .

OTHER PUBLICATIONS

Morrison et al.; *Organic Chemistry*, pp. 525 and 590, (1969).

*Primary Examiner*—Mary C. Lee
*Attorney, Agent, or Firm*—Armstrong, Nikaido, Marmelstein & Kubovcik

[57] ABSTRACT

A process is disclosed wherein an optically active N-mercaptoalkanoylamino acid is prepared by (1) reacting an optically active $\beta$-hydroxyalkanoic acid, with a halogenating reagent to prepare an optically active $\beta$-haloalkanoyl halide (2) reacting the $\beta$-haloalkanoyl halide with an amino acid to produce an optically active N-$\beta$-haloalkanoylamino acid and (3) reacting the N-$\beta$-haloalkanoylamino acid with a reagent capable of converting the halogen into the thiol group, the configuration of the formulas (II), (III), (IV), (V), and (VI) being retained in all the optically active compounds throughout the process to prepare the compound represented by formula (I). The product of the present invention, for example, N-(3-mercapto-2-D-methylpropanoyl)-L-proline inhibits the enzymatic conversion of angiotensin I into angiotensin II and therefore is useful for relieving angiotensin-related hypertension.

17 Claims, No Drawings

PROCESS FOR PREPARATION OF OPTICALLY ACTIVE N-MERCAPTOALKANOYLAMINO ACIDS

BRIEF SUMMARY OF THE INVENTION

The present invention relates to a process for preparation of optically active N-mercaptoalkanoylamino acids. More specifically, the present invention relates to a process for preparing optically active N-mercaptoalkanoylamino acids represented by formula (I):

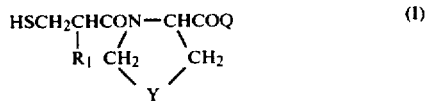

wherein $R_1$ is lower alkyl having from 1 to 4 carbon atoms, Y is $(CH_2)_n$ (n=1 or 2) or sulfur, and Q is hydroxy or residual part of an amino acid represented by formula (II):

wherein $R_2$ is lower alkyl having from 1 to 4 carbon atoms or benzyl, starting from an optically active β-hydroxyalkanoic acid represented by formula (III):

wherein $R_1$ is the same as defined above.

The product of the present invention inhibits the enzymatic conversion of angiotensin I into angiotensin II and therefore is useful for relieving angiotensin-related hypertension. Potency of N-mercaptoalkanoylamino acids, such as N-(3-mercapto-2-D-methylpropanoyl)-L-proline which is considered the most prospective as a hypotensive drug, critically depends on the configuration of the mercaptoalkanoyl side chain of the compounds [M. A. Ondetti et al., Biochemistry, 16, 5484 (1977); The Medical Journal of Australia, Vol. 2, p. 1 et seq. "Symposium on Converting Enzyme Inhibition in Hypertension", (1979)]. The compound specified above with L configuration in the mercaptoalkanoyl side chain is about 100 times less inhibitory against the enzyme than the corresponding D-enantiomer. The preparation of D-enantiomer of N-mercaptoalkanoylamino acids, for example, N-(3-mercapto-2-D-methylpropanoyl)-L-proline, has thus far involved a troublesome optical resolution as an inevitable step because optically inactive starting materials have been used for their production [M. A. Ondetti et al., U.S. Pat. No. 4,046,889 (1977); U.S. Pat. No. 4,105,776 (1978); U.S. Pat. No. 4,154,840 (1979)]. Moreover, the known processes for their production include the reaction of an N-ω-haloalkanoylamino acid with an anion of a thioacid such as thiolacetic acid or thiobenzoic acid in order to produce an N-acylthioalkanoylamino acid; therefore, the acyl group as a protecting group for the thiol group must finally be removed to obtain the desired N-mercaptoalkanoylamino acid. The deprotection is conducted in an alkaline solution; however, under such conditions, the thiol compound liberated is liable to be oxidized yielding the disulfide which must be reconverted into the thiol compound by reducing it with, e.g., zinc power in a diluted mineral acid. For these reasons, known processes for producing optically active N-mercaptoalkanoylamino acids are complicated. Thus more simplified process, especially unaccompanied by optical resolution, has been hoped for.

The object of the present invention is therefore to provide an improved process for preparing an optically active N-mercaptoalkanoylamino acid.

The present inventors carried out researches in order to establish an improved process for preparing an optically active N-mercaptoalkanoylamino acid and have now completed the present invention.

The present invention is a process for preparation of an optically active N-mercaptoalkanoylamino acid represented by formula (I):

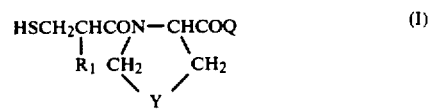

wherein $R_1$ is lower alkyl having from 1 to 4 carbon atoms, Y is $(CH_2)_n$ (n=1 or 2) or sulfur, and Q is hydroxy or residual part of an amino acid represented by formula (II):

wherein $R_2$ is lower alkyl having from 1 to 4 carbon atoms or benzyl,
which comprises (1) reacting an optically active β-hydroxyalkanoic acid represented by formula (III):

wherein $R_1$ is the same as defined above, with a halogenating reagent to prepare an optically active β-haloalkanoyl halide represented by formula (IV):

wherein X is halogen and $R_1$ is the same as defined above;

(2) reacting the β-haloalkanoyl halide with an amino acid represented by formula (V):

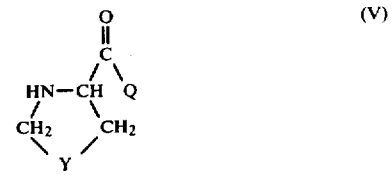

wherein Y and Q are the same as defined above, to produce an optically active N-β-haloalkanoylamino acid represented by formula (VI):

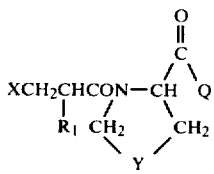

wherein X, R₁, Y, and Q are the same as defined above; and (3) reacting the N-β-haloalkanoylamino acid with a reagent capable of converting the halogen into the thiol group, the configuration of the formulas (II), (III), (IV), (V), and (VI) being retained in all the optically active compounds throughout the process to prepare the compound represented by formula (I).

According to the present invention, an optically active N-mercaptoalkanoylamino acid (I) can be obtained starting from an optically active β-hydroxyalkanoic acid (III) in a simple process which involves neither the step of optical resolution nor the step of protection of the thiol group as explained hereinbefore. It is an advantageous feature of the present invention that the configuration of all the optically active compounds involved in the process is retained throughout the process.

The starting materials of the present invention, the compound (III), have come to be produced industrially according to inventions by some of the present inventors in which the compound (III) is produced by subjecting the corresponding alkanoic acid to the stereospecific action of microorganisms. In particular, the compound (III) in which R₁ is methyl, can be produced by subjecting isobutyric acid or methacrylic acid to the stereospecific action of specific microorganisms [Japanese patent applications Nos. 144252/1979, 144253/1979, 17559/1980, 103805/1980, 140258/1980, 140259/1980, and 141453/1980].

In one aspect, therefore, the present invention is very advantageous in that the starting material is readily available industrially and the optical activity thereof can be retained to produce the desired optically active product. Thus the present invention has eliminated the foregoing drawbacks of known processes, thus providing an advantageous process for preparing an optically active N-mercaptoalkanoylamino acids.

Concerning halogenation of hydroxyalkanoic acid which relates to the first step of the process of the present invention, it was reported that thionyl chloride was allowed to act on α-hydroxyisobutyric acid [E. E. Blaise and M. Montagne, Compt. rend., 174, 1553 (1922)]; however, the product of the reaction was not α-chloroisobutyryl chloride but was anhydrosulfite of α-hydroxyisobutyric acid and, moreover, there are no description of optical activity in the report. In another report [E. L. Eliel et al., Org. Synth., Coll. Vol. IV, p. 169 (1963)], optically active α-chlorophenylacetic acid was produced from mandelic acid according to a two-step process in which the carboxyl group was first protected by esterification with ethanol and then halogenation with thionyl chloride was conducted, the aimed free acid finally being obtained by hydrolysis of the ester group.

In contrast with these known halogenation of hydroxyalkanoic acids, it is to be noted that, in the process of the present invention, halogenation of an optically active β-hydroxyalkanoic acid (III) can be performed on both the hydroxyl group and the carboxyl group in one step with retention of the configuration to produce an optically active β-haloalkanoyl halide (IV).

The conversion of the halogen in the compound (VI) into the thiol group in the third step of the process of the present invention is conducted with the usual reagents capable of converting the halogen into the thiol group [P. Klason and T. Carlson, Chem. Ber., 39, 732 (1906); Fore a review of the reaction, see Methoden der Organischen Chemie (Houben-Weyl), Vol. 9, p. 7 et seq. (1955)]. On the other hand, there are no previous examples concerning the application of such reagents to the conversion of a halogen into the thiol group in an optically active compound such as the compound (VI) of the process of the present invention. In general, the reagent, e.g., sodium hydrosulfide or ammonium hydrosulfide is strongly alkaline in solution and therefore no one has ever tried the application of the reagent to an optically active compound because racemization is expected to take place readily under such alkaline conditions.

Nevertheless, we have surprisingly found that the optical activity is retained sufficiently in the reaction of the compound (VI) with an alkaline reagent such as sodium hydrosulfide and ammonium hydrosulfide and, moreover, side reactions can be minimized. Moreover, in the present process, there is no need for protection of the thiol group and subsequent deprotection thereof which have been inevitable in hitherto known methods of converting a halogen group into the thiol group.

DETAILED DESCRIPTION OF THE INVENTION

The lower alkyl groups having from 1 to 4 carbon atoms represented by R₁ in compounds (I), (III), (IV), and (VI) include straight and branched chain hydrocarbon groups such as methyl, ethyl, propyl, isopropyl, butyl, isobutyl, t-butyl, and so forth. Preferred compounds for medicinal uses among the compound (I) are those wherein R₁ is methyl and Y is CH₂, and R₁ is methyl and Y is sulfur; especially preferred are those wherein R₁ is methyl, Y is CH₂, and Q is hydroxy; R₁ is methyl, Y is CH₂, and Q is residual part of an amino acid (II) wherein R₂ is benzyl; and R₁ is methyl, Y is sulfur, and Q is hydroxy.

The residual part of an amino acid represented by formula (II) include residual parts of alanine, glycine, valine, leucine, isoleucine, and phenylalanine, preferably phenylalanine.

According to the process of the present invention, the optically active β-hydroxyalkanoic acid (III) can readily be converted into the optically active β-haloalkanoyl halide (IV) with retention of the optical activity in a one-step reaction as described hereinbefore. As described above in comparison with known methods for halogenation of hydroxyalkanoic acids, this step in the process of the present invention is the first facile method for preparing an optically active β-haloalkanoyl halide from an optically active β-hydroxyalkanoic acid with retention of the optical activity in one step reaction.

The halogenation of the optically active β-hydroxyalkanoic acid (III) is conducted preferably in the presence of a catalyst such as an organic amine, acid addition salt thereof, or acid amide. As the organic amine is used, for example, methylamine, dimethylamine, trimethylamine, ethylamine, diethylamine, triethylamine, imidazole, piperidine, morpholine, pyridine, N,N-dimethylaniline, or N,N-diethylaniline. Imidazole is the most preferable among these. A hydrochloride, hydrobromide, sulfate, or phosphate is used as an acid addition salt of the organic amine. As the acid amide is used, for example, formamide, N-methylformamide, N,N-dimethylformamide, acetamide, N,N-dimethylacetamide, N-formylmorpholine, or N-formylpiperidine. In the halogenation, the molar ratio of the catalyst to the β-hydroxyalkanoic acid (III) is from about 0.0001 to about 0.1, preferably from about 0.0001 to about 0.05. The halogenating reagent is, for example, thionyl chloride or thionyl bromide. The molar ratio of the halogenating reagent to the β-hydroxyalkanoic acid (III) is from about 2 to about 3, preferably from about 2 to about 2.2. The halogenation can be conducted without a solvent; however, the use of an inert organic solvent, such as diethyl ether, tetrahydrofuran, methylene chloride, ethylene dichloride, chloroform, carbon tetrachloride, benzene, and toluene, makes the reaction controllable. In the halogenation, the temperature control is important to minimize side reactions and to retain the configuration of the starting β-hydroxyalkanoic acid (III). The reactants, that is, the halogenating reagent and the compound (III), are mixed while the temperature of the reaction mixture is kept at not more than 25° C. Then, after completion of the mixing, the temperature of the resulting reaction mixture is raised up to from about 30° C. to about 100° C., preferably to from about 70° C. to about 80° C. to complete the reaction. The mixing of the two reactants described above can be carried out by adding by drops either of the two reactants to the other.

The product of the halogenation reaction, an optically active β-haloalkanoyl halide (IV), is subjected to a coupling reaction with an amino acid (V), yielding an optically active N-β-haloalkanoylamino acid (VI). This coupling reaction is effected in an alkaline medium, such as a dilute aqueous solution of an alkali metal hydroxide, alkali metal bicarbonate, or alkali metal carbonate solution at a low temperature, e.g., about from 0° C. to about 15° C.

The product, an optically active N-β-haloalkanoylamino acid (VI), is then subjected to a displacement reaction of the halogen atom by the thiol group, yielding the disired product of the present invention, an optically active N-mercaptoalkanoylamino acid (I). As described hereinbefore, also in this reaction, the configuration of the compound (VI) is retained. The reagent capable of converting the halogen into the thiol group is, for example, a salt of hydrogen sulfide with an alkali or alkaline earth metal, ammonia, or an organic base, preferably sodium hydrosulfide or ammonium hydrosulfide. The organic base includes methylamine, dimethylamine, trimethylamine, ethylamine, diethylamine, triethylamine, pyridine, piperidin, morpholine, and imidazole, and so forth. Methylamine is preferable among the organic bases. The displacement reaction of the halogen by the thiol group is carried out in water or in a polar aprotic solvent such as dimethyl sulfoxide, N,N-dimethylformamide, and N,N-dimethylacetamide. The reagents, described above, which are capable of converting the halogen into the thiol group are all strongly alkaline in water or in the polar aprotic solvent, but neither the compound (VI) nor the compound (I) undergoes racemization in this reaction. This is noteworthy since an optically active compound generally undergoes racemization in an alkaline solution. Further, there have thus far been no reports on displacement of a halogen atom of an optically active compound by a salt of hydrogen sulfide.

The desired product of this invention, the compound (I), obtained in the foregoing final step of the process is very susceptible to oxidation and liable to be oxidized to give the disulfide represented by the following formula:

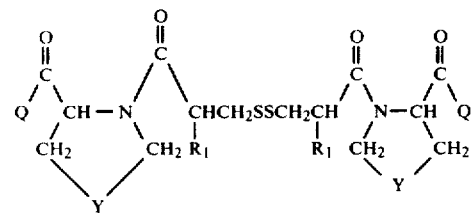

wherein $R_1$, Y, and Q are the same as defined above, which can be reverted to the thiol compound (I) with the usual reducing reagent, e.g., zinc powder in a dilute mineral acid, and sodium hydrosulfite. Another by-product of the final step of the process is the sulfide of the following formula:

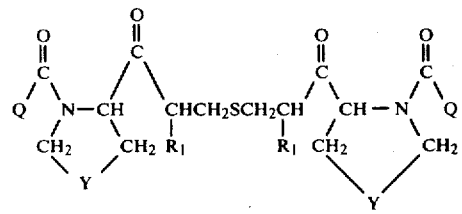

wherein $R_1$, Y, and Q are the same as defined above, which can hardly be converted into the thiol compound (I).

We have found that the side reactions can be averted by adopting the optimum molar ratio of the salt of hydrogen sulfide to the N-β-haloalkanoyl amino acid (VI). The optimum molar ratio is from about 2 to about 10, preferably from about 4 to about 6.

The concentration of the salt of hydrogen sulfide in the reaction system is also an important factor in minimizing the amount of by-products. The optimum concentration is from about 5 wt% to about 10 wt%. The reaction in an inert gas atomsphere is effective in minimizing the amount of the disulfide described above. The reaction is carried out at a temperature of from about 30° C. to about 100° C., preferably from about 60° C. to about 90° C., under which conditions no racemization occurs.

According to a preferred process for preparing the compound of formula (I), especially when $R_1$ is methyl, X is chlorine, Y is $CH_2$, and Q is hydroxy, the β-hydroxyalkanoic acid of formula (III) is halogenated with thionyl halide, preferably thionyl chloride, in an anhydrous inert organic solvent, preferably methylene chloride or toluene, in the presence of a catalyst, preferably imidazole, of which the molar ratio to the acid of formula (III) is from about 0.0001 to about 0.05, keeping the temperature of the reaction mixture at not more than 25° C. during the addition of the thionyl halide to the acid of formula (III) and then raising the temperature of the reaction mixture up to from about 70° C. to about 80° C. over a period of an hour to prepare the β-haloalkanoyl halide of formula (IV), which is isolated by distillation under reduced pressure. The halide of formula (IV) is then coupled with the amino acid of formula (V) by a conventional method in which the coupling is effected in an alkaline medium, e.g., a dilute solution of an alkali metal hydroxide at a low temperature, e.g., from about 0° C. to about 15° C., yielding the β-haloalkanoylamino acid of formula (VI). Subsequently, the product is reacted with a reagent capable of converting the halogen into the thiol group, preferably sodium hydrosulfide or ammonium hydrosulfide, of which the molar ratio to the β-haloalkanoylamino acid of formula (VI) is from about 4 to about 6, in water or a polar aprotic solvent, preferably in water, at a temperature of from about 60° C. to about 90° C. to produce the N-mercaptoalkanoylamino acid of formula (I).

To further illustrate the present invention, and not by way of limitation, the following examples are given.

EXAMPLE 1

3-Chloro-2-D-methylpropanoyl chloride from 3-hydroxy-2-D-methylpropanoic acid

To a mixture of 3-hydroxy-2-D-methylpropanoic acid (36.6 g) and N,N-dimethylformamide (1.28 g), thionyl chloride (92.0 g) was added by drops with stirring over a period of 90 min, while the temperature of the reaction mixture was kept at not more than 25° C. by cooling in an ice-water bath. The reaction mixture was then warmed up to 40° C. and kept at that temperature for 1 hr. After removal of an excess of thionyl chloride by evaporation in a vacuum, 3-chloro-2-D-methylpropanoyl chloride was obtained as a colorless liquid by distillation under reduced pressure (32.1 g, 65%). bp 53°–54° C./21 mmHg. $[\alpha]_D^{25} -4.8°$ (C 2.0, $CH_2Cl_2$).

EXAMPLE 2

3-Chloro-2-D-methylpropanoyl chloride

To a solution of 3-hydroxy-2-D-methylpropanoic acid (10.4 g) in methylene chloride (10 ml) containing imidazole (0.5 g) as catalyst, thionyl chloride (30 g) was added by drops with stirring at a temperature of from about 0° C. to about 15° C. The reaction mixture was worked up in the same manner as in Example 1, yielding 3-chloro-2-D-methylpropanoyl chloride (11.7 g, 83%). bp 65°–67° C./34 mmHg.

EXAMPLE 3

3-Chloro-2-D-methylpropanoyl chloride

By substituting toluene for methylene chloride and heating the reaction mixture at a temperature of 90° C. for 1 hr after addition of thionyl chloride in the procedure of Example 2, 3-chloro-2-D-methylpropanoyl chloride was obtained (85%).

EXAMPLE 4

3-Bromo-2-D-methylpropanoyl bromide

By substituting thionyl bromide for thionyl chloride in the procedure of Example 3, 3-bromo-2-D-methylpropanoyl bromide was obtained.

EXAMPLE 5

3-Chloro-2-L-methylpropanoyl chloride

By substituting the L-enantiomer for 3-hydroxy-2-D-methylpropanoic acid in the procedure of Example 2, 3-chloro-2-L-methylpropanoyl halide was obtained. $[\alpha]_D^{25} +4.7°$ (C 2.0, $CH_2Cl_2$).

EXAMPLE 6

3-Chloro-2-L-ethylpropanoyl chloride

By substituting 3-hydroxy-2-L-ethylpropanoic acid for 3-hydroxy-2-D-methylpropanoic acid in the procedure of Example 2, 3-chloro-2-L-ethylpropanoyl chloride was obtained. bp 50°–52° C./40 mmHg. $[\alpha]_D^{25} -3.8°$ (C 2.0, $CH_2Cl_2$).

EXAMPLE 7

N-(3-chloro-2-D-methylpropanoyl)-L-proline

To a cold solution of L-proline (4.08 g) in an aqueous 2 N sodium hydroxide solution (35.5 ml), 3-chloro-2-D-methylpropanoyl chloride (5.0 g) was added. The resulting mixture was stirred at room temperature for 4 hr. Then, the reaction mixture, adjusted to pH 2 with phosphoric acid, was extracted with ethyl acetate (total 60 ml, twice). The ethyl acetate extract was washed with a saturated aqueous solution of sodium chloride and dried over anhydrous sodium sulfate. Removal of the solvent from the extract left N-(3-chloro-2-D-methylpropanoyl)-L-proline as a white solid, which was recrystallized from ethyl acetate-n-hexane (40 ml-40 ml) to yield 6.6 g of the crystals (85%). mp 124°–126° C. $[\alpha]_D^{25} -101.5°$ (C 2.0, EtOH).

EXAMPLE 8

N-(3-mercapto-2-D-methylpropanoyl)-L-proline

A solution of N-(3-chloro-2-D-methylpropanoyl)-L-proline (0.5 g) and sodium hydrosulfide dihydrate (0.84 g) in water (6 ml) was warmed with stirring at about 80° C. for 4 hr under nitrogen atmosphere, when no starting halide was detected on thin layer chromatogram [Merck Kieselgel 60, F-254, Rf of the halide is 0.56 and that of the product, N-(mercapto-2-D-methylpropanoyl)-L-proline, is 0.58]. The reaction mixture was diluted with cold water (10 ml), adjusted to pH 1 with sulfuric acid, and treated with zinc powder (0.5 g) as reducing agent by stirring at room temperature for 4 hr under nitrogen atmosphere, whereby the by-produced disulfide (ca. 5 mole %) was reduced to N-(3-mercapto-2-D-methylpropanyl)-L-proline. Insoluble materials were filtered off from the reaction mixture and washed with fresh methanol. The filtrate, combined with the washings, was evaporated to remove the methanol. The residual aqueous solution was extracted with ethyl acetate (50 ml × 3). The ethyl acetate extract was washed with a saturated aqueous solution of sodium chloride and dried over anhydrous magnesium sulfate. Removal of the solvent from the extract left colorless syrup (0.47 g), which was recrystallized from ethyl acetate-n-hexane (2 ml-2 ml) to give white crystals of N-(3-mercapto-2-D-methylpropanoyl)-L-proline (0.35 g, 71%). mp 84°–85° C. $[\alpha]_D^{25} -128.5°$ (C 1.7, EtOH). Anal. Calc'd for $C_9H_{15}NO_3S$: C; 49.75, H; 6.96, N; 6.45, Found: C; 49.66, H; 6.92, N; 6.40.

EXAMPLE 9

N-(3-mercapto-2-D-methylpropanoyl)-L-proline

A solution of N-(3-chloro-2-D-methylpropanoyl)-L-proline (0.5 g) and sodium hydrosulfide dihydrate (0.63 g) in N,N-dimethylformamide (4 ml) was warmed with stirring at 50° C. for 4 hr under nitrogen atmosphere. The reaction mixture was diluted with cold water (40 ml), adjusted to pH 1 with 6 N hydrochloric acid, and extracted with ethyl acetate (50 ml × 3). The ethyl acetate extract was worked up in the same manner as in Example 8, giving crystals of N-(3-mercapto-2-D-methylpropanoyl)-L-proline (0.32 g, 65%).

EXAMPLE 10

N-(3-mercapto-2-D-methylpropanoyl)-L-proline

To an aqueous solution of ammonium hydrosulfide prepared by saturating a 0.25 M aqueous ammonium hydroxide solution (20 ml) with hydrogen sulfide at room temperature, N-(3-chloro-2-D-methylpropanoyl)-L-proline (1.0 g) was added. The resulting mixture was warmed with stirring at 90° C. for 20 hr. The conversion of the halide into the thiol compound was followed by observing the NMR spectrum at intervals. The reaction mixture was then concentrated to about 20 ml, adjusted to pH 1 with 6 N hydrochloric acid, and extracted with ethyl acetate (100 ml+50 ml). The ethyl acetate extract was worked up in the same manner as in Example 8, and the resulting colorless syrup (1.1 g) was chromatographed on a long (L/D=80) column of silica gel (Wakogel C200: a trademark of Wako Pure Chemical Industries, Ltd.) eluting with a linear gradient of from 0% to 80% methanol in ethyl acetate (v/v). Fractions containing the desired product, N-(3-mercapto-2-D-methylpropanoyl)-L-proline, were pooled and concentrated to dryness under reduced pressure. Recrystallization of the resulting residue from ethyl acetate-cyclohexane (4 ml-2 ml) afforded the pure product (0.91 g, 92%). From other fractions, the disulfide (60 mg, 6.1%), $[\alpha]_D^{25}-248.6°$ (C 1, MeOH), and the sulfide (5 mg, 0.5%), $[\alpha]_D^{25}-101.8°$ (C 2, EtOH) were isolated.

EXAMPLE 11

N-(3-mercapto-2-D-methylpropanoyl)-L-proline

An aqueous solution of ammonium hydrosulfide was prepared by saturating 0.5 M ammonium hydroxide solution (100 ml) with hydrogen sulfide at room temperature. In this solution was dissolved N-(3-chloro-2-D-methylpropanoyl)-L-proline (1.0 g). The resulting mixture was warmed with stirring at 90° C. for 16 hr, when no starting halide was detected on the NMR spectrum. The reaction mixture was worked up in the same manner as in Example 10, giving white crystals of the desired product, N-(3-mercapto-2-D-methylpropanoyl)-L-proline (0.85 g, 86%). The by-produced disulfide (102 mg, 10%) and sulfide (10 mg, 1%) were also isolated.

EXAMPLE 12

N-(3-chloro-2-L-methylpropanoyl)-L-proline

By substituting 3-chloro-2-L-methylpropanoyl chloride for the D-enantiomer in the procedure of Example 7, N-(3-chloro-2-L-methylpropanoyl)-L-proline was obtained.

EXAMPLE 13

N-(3-mercapto-2-L-methylpropanoyl)-L-proline

By treating the product of Example 12 with ammonium hydrogen-sulfide in the same manner as in Example 11, N-(3-mercapto-2-L-methylpropanoyl)-L-proline was obtained. mp 104°–105° C. $[\alpha]_D^{22}-41.0°$ (C 2.0, EtOH).

EXAMPLE 14

N-(3-chloro-2-D-methylpropanoyl)-L-thiazolidine-4-carboxylic acid

By substituting 4-L-thiazolidine carboxylic acid for L-proline in the procedure of Example 7, N-(3-chloro-2-D-methylpropanoyl)-L-thiazolidine-4-carboxylic acid was obtained as white crystals. mp 138°–140° C. $[\alpha]_D^{22}-130.1°$ (C 2.0, EtOH).

EXAMPLE 15

N-(3-mercapto-2-D-methylpropanoyl)-L-thiazolidine-4-carboxylic acid

By substituting N-(3-chloro-2-D-methylpropanoyl)-L-thiazolidine-4-carboxylic acid for N-(3-chloro-2-D-methylpropanoyl)-L-proline in the procedure of Example 10, N-(3-mercapto-2-D-methylpropanoyl)-L-thiazolidine-4-carboxylic acid was obtained as white crystals. mp 113°–114° C. $[\alpha]_D^{25}-172.0°$ (C 1.0, MeOH). Anal. Calc'd for $C_8H_{13}NO_3S_2$: C; 40.83, H; 5.57, N; 5.95, Found: C; 40.74, H; 5.53, N; 5.90.

EXAMPLE 16

N-(3-chloro-2-D-methylpropanoyl)-L-prolyl-D-phenylalanine

By substituting L-prolyl-D-phenylalanine for L-proline in the procedure of Example 7, N-(3-chloro-2-D-methylpropanoyl)-L-prolyl-D-phenylalanine was obtained.

EXAMPLE 17

N-(3-mercapto-2-D-methylpropanoyl)-L-prolyl-D-phenylalanine

By substituting N-(3-chloro-2-D-methylpropanoyl)-L-prolyl-D-phenylalanine for N-(3-chloro-2-D-methylpropanoyl)-L-proline in the procedure of Example 9, N-(3-mercapto-2-D-methylpropanoyl)-L-prolyl-D-phenylalanine was obtained.

EXAMPLE 18

N-(3-mercapto-2-D-methylpropanoyl)-L-proline from 3-chloro-2-D-methylpropanoyl chloride.

To a cold solution of L-proline (0.4 g) in an aqueous 2 N sodium hydroxide (3.5 ml), 3-chloro-2-D-methylpropanoyl chloride (0.5 g) was added. The resulting mixture was stirred at room temperature for 4 hr. Then a 10 M ammonium hydroxide solution (3.42 ml) and water (7 ml) were added to the mixture. Hydrogen sulfide was introduced into the mixture until saturation (0.9 g was dissolved) at room temperature. The reaction mixture was warmed at 80° C. for 15 hr with stirring under nitrogen atmosphere. After removal of the excessive ammonium hydrosulfide by evaporation under reduced pressure, the residual aqueous solution was worked up in the same manner as in Example 10 to give the desired product, N-(3-mercapto-2-D-methylpropanoyl)-L-proline (690 mg, 91.4%). The disulfide (39 mg, 2.6%) and the sulfide (24 mg, 1.7%) were also isolated.

In addition to the reactants and conditions used in the examples, other reactants and conditions as set forth in the specification may also be used to obtain substantially the same results. Particularly, in cases in which Q in the desired product (I) (D-, or L-enantiomer) in the specification is residual part of an amino acid (II) (D-, or L-enantiomer) in the specification, compounds listed in Table 1 below, for example, can be prepared in substantially the same manner as in Example 16 and 17.

TABLE 1

| | Examples of Compound (I) (D-, or L-enantiomer) | | |
|---|---|---|---|
| No. | R₁ | Y | R₂ |
| 1 | CH₃ | CH₂ | CH₃ |
| 2 | CH₃ | S | CH₃ |
| 3 | CH₃ | S | CH₃ |
| 4 | CH₃ | CH₂ | CHCH₂CH₃<br>\|<br>CH₃ |
| 5 | CH₃ | CH₂ | CH₂CH(CH₃)(CH₃) |
| 6 | CH₃ | CH₂CH₂ | CH₂C₆H₅ |
| 7 | CH₂CH₃ | CH₂ | CH₂C₆H₅ |
| 8 | CH₂CH₃ | S | CH₂C₆H₅ |
| 9 | CH₂CH₃ | CH₂ | CH₃ |
| 10 | HC(CH₃)(CH₃) | CH₂ | CH₂C₆H₅ |
| 11 | HC(CH₃)(CH₃) | S | CH₂C₆H₅ |

It is also a characteristic feature of the process of the present invention that an intermediate, N-β-haloalkanoylamino acid, need not be isolated for further treatment as seen from Example 18; thus, the procedures can be simplified as compared with known methods.

What is claim is:

1. A process for the preparation of an optically active N-mercaptoalkanoylamino acid represented by formula (I):

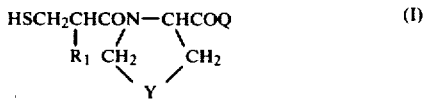

(I)

wherein R₁ is lower alkyl having from 1 to 4 carbon atoms, Y is (CH₂)ₙ, n being 1 or 2, or sulfur, and Q is hydroxy or the residual part of an amino acid represented by formula (II):

$$-HNCHCO_2H \atop R_2$$ (II)

wherein R₂ is lower alkyl having from 1 to 4 carbon atoms or benzyl, which comprises (1) reacting an optically active β-hydroxyalkanoic acid represented by formula (III):

(III)

wherein R₁ is the same as defined above, with thionyl chloride or thionyl bromide in the presence of a catalyst by keeping the temperature of the reaction mixture at not more than 25° C. when said thionyl chloride or thionyl bromide is mixed with the compound (III) and then raising the temperature of the reaction mixture up to from about 30° C. to about 100° C. to prepare an optically active β-haloalkanoyl halide represented by formula (IV):

(IV)

wherein X is chlorine or bromine and R₁ is the same as defined above;

(2) reacting the β-haloalkanoyl halide with an amino acid represented by formula (V):

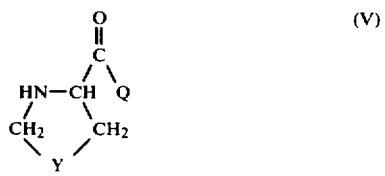

(V)

wherein Y and Q are the same as defined above, to produce an optically active N-β-haloalkanoylamino acid represented by formula (VI):

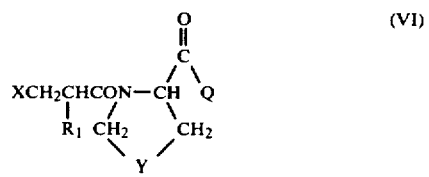

(VI)

wherein X, R₁, Y and Q are the same as defined above; and (3) reacting the N-β-haloalkanoylamino acid with an alkali metal salt of hydrogen sulfide or ammonium hydrosulfide, of which the molar ratio to the compound (VI) is from about 2 to about 10, in water or a polar aprotic solvent at a temperature of from about 60° C. to about 90° C., the configuration of the formulas (II), (III), (IV), (V), and (VI) being retained in all the optically active compounds throughout the process to prepare the compound represented by formula (I).

2. The process according to claim 1 wherein R₁ is methyl, Y is CH₂, and Q is hydroxy.

3. The process according to claim 1 wherein R₁ is methyl, Y is sulfur, and Q is hydroxy.

4. The process according to claim 1 wherein R₁ is methyl, Y is CH₂, and Q is the residual part of an amino acid (II) wherein R₂ is benzyl.

5. The process according to claim 1 wherein the molar ratio of the catalyst to the compound (III) is from about 0.0001 to about 0.1.

6. The process according to claim 1 wherein the catalyst is an organic amine or an acid addition salt thereof.

7. The process according to claim 6 wherein the organic amine is methylamine, dimethylamine, trimethylamine, ethylamine, diethylamine, triethylamine, imidazole, piperidine, morpholine, pyridine, N,N-dimethylaniline, or N,N-diethylaniline.

8. The process according to claim 1 wherein the catalyst is an organic acid amide.

9. The process according to claim 8 wherein the organic acid amide is formamide, N-methylformamide, N,N-dimethylformamide, acetamide, N,N-dimethylacetamide, N-formylmorpholine, or N-formylpiperidine.

10. The process according to claim 1 wherein the molar ratio of thionyl chloride or thionyl bromide to the compound (III) is from about 2 to about 3.

11. The process according to claim 1 wherein the halogenation of the compound (III) is carried out in an inert organic solvent.

12. The process according to claim 11 wherein the inert organic solvent is diethyl ether, tetrahydrofuran, methylene chloride, ethylene dichloride, chloroform, carbon tetrachloride, benzene, or toluene.

13. The process according to claim 1 wherein the polar aprotic solvent is dimethyl sulfoxide, N,N-dimethylformamide, or N,N-dimethylacetamide.

14. The process according to claim 1 wherein the concentration of the alkali metal salt of hydrogen sulfide in the reaction system is from about 5 wt % to about 10 wt %.

15. The process according to claim 1, wherein the conversion of the halogen in the compound (VI) into the thiol group is carried out in an inert gas atmosphere.

16. The process according to claim 1 wherein the optically active β-hydroxyalkanoic acid (III) is prepared by subjecting the corresponding alkanoic acid to the action of a microorganism having the ability to convert the alkanoic acid into the optically active β-hydroxyalkanoic acid (III).

17. The process according to claim 2 wherein the optically active β-hydroxyalkanoic acid (III) is prepared by subjecting isobutyric acid or methacrylic acid to the action of a microorganism having the ability to convert isobutyric acid or methacrylic acid into the optically active β-hydroxyalkanoic acid (III).

* * * * *